United States Patent
Balzar

[19]

[11] Patent Number: 5,827,256
[45] Date of Patent: Oct. 27, 1998

[54] TAMPON HAVING A PROTECTIVE FINGER SHEATH AND A METHOD OF FORMING

[75] Inventor: Tammy Jo Balzar, Menasha, Wis.

[73] Assignee: Kimberly-Clark Worldwide, Inc, Neenah, Wis.

[21] Appl. No.: 730,540

[22] Filed: Oct. 11, 1996

Related U.S. Application Data

[63] Continuation-in-part of Ser. No. 426,393, Apr. 21, 1995, abandoned.

[51] Int. Cl.$^6$ .............................. A61F 13/15; A61F 13/20
[52] U.S. Cl. ......................... 604/385.1; 604/904; 28/118
[58] Field of Search ..................... 604/11–118, 285–288, 604/363, 904, 385.1, 377; 28/118–120

[56] References Cited

U.S. PATENT DOCUMENTS

| | | |
|---|---|---|
| 1,932,383 | 10/1933 | Richardson . |
| 2,733,714 | 2/1956 | Haas . |
| 3,058,469 | 10/1962 | Crockford . |
| 3,135,262 | 6/1964 | Kobler et al. . |
| 3,358,686 | 12/1967 | Asaka . |
| 3,674,029 | 7/1972 | Bates et al. . |
| 3,683,912 | 8/1972 | Olson et al. . |
| 3,732,866 | 5/1973 | Accavallo . |
| 3,854,481 | 12/1974 | Messing . |
| 3,881,485 | 5/1975 | Davis, Jr. . |
| 3,946,737 | 3/1976 | Kobler . |
| 4,027,673 | 6/1977 | Poncy et al. . |
| 4,041,948 | 8/1977 | Flam et al. . |
| 4,165,942 | 8/1979 | Johansson ................. 401/132 |
| 4,661,101 | 4/1987 | Sustmann ................. 604/360 |
| 4,795,422 | 1/1989 | Conner et al. ............. 604/14 |
| 4,951,368 | 8/1990 | Heinen ..................... 28/118 |
| 5,006,116 | 4/1991 | Alikhan et al. ........... 604/365 |
| 5,084,038 | 1/1992 | Sheldon et al. ........... 604/358 |
| 5,135,475 | 8/1992 | Nakanishi et al. ........ 604/14 |
| 5,158,535 | 10/1992 | Paul et al. ................ 604/15 |
| 5,185,010 | 2/1993 | Brown, Jr. ................ 604/379 |
| 5,282,789 | 2/1994 | Lundy ..................... 604/55 |
| 5,403,300 | 4/1995 | Howarth .................. 604/384 |

FOREIGN PATENT DOCUMENTS

| | | |
|---|---|---|
| 0 104 039 | 3/1984 | European Pat. Off. . |
| 656 610 | 2/1938 | Germany . |
| 1 018 586 | 5/1955 | Germany . |
| 93641 | 2/1960 | Netherlands . |
| 202 109 | 11/1937 | Switzerland . |
| 710 670 | 6/1954 | United Kingdom . |
| 2 227 666 | 8/1990 | United Kingdom . |

OTHER PUBLICATIONS

Photocopy of Japanese Finger Sheath with instructions in Japanese and translated into English.

*Primary Examiner*—John G. Weiss
*Assistant Examiner*—K. M. Reichle
*Attorney, Agent, or Firm*—Thomas J. Connelly

[57] ABSTRACT

A tampon having a protective finger sheath is disclosed along with a method of forming the tampon. The tampon is constructed from an absorbent having a first end and a second end. An L-shaped cover having a leg, a foot and a central longitudinal axis is aligned with the absorbent such that the foot is aligned adjacent to the second end of the absorbent. Both the absorbent and the cover are rolled or wound up along a central longitudinal axis of the absorbent-cover combination into a cylindrically shaped softwind which is compressed into an absorbent pledget. The absorbent pledget has a predetermined diameter, an insertion end and a trailing end, and a flexible sheath which extends outward from the trailing end. The flexible sheath is sized to receive a user's finger and prevent soiling of the finger during insertion of the absorbent pledget into a body cavity. The flexible sheath also enables the absorbent pledget to be removed from the body cavity in a clean and easy manner. The method of forming the tampon is also disclosed. The method includes forming an absorbent ribbon having a predetermined width. Positioning the absorbent ribbon over a cover such that a portion of the cover extends beyond the width of the absorbent ribbon. The absorbent ribbon and the cover are then cut to a desired length and both materials are rolled into a cylindrically shaped softwind. The softwind is then compressed into an absorbent pledget.

29 Claims, 6 Drawing Sheets

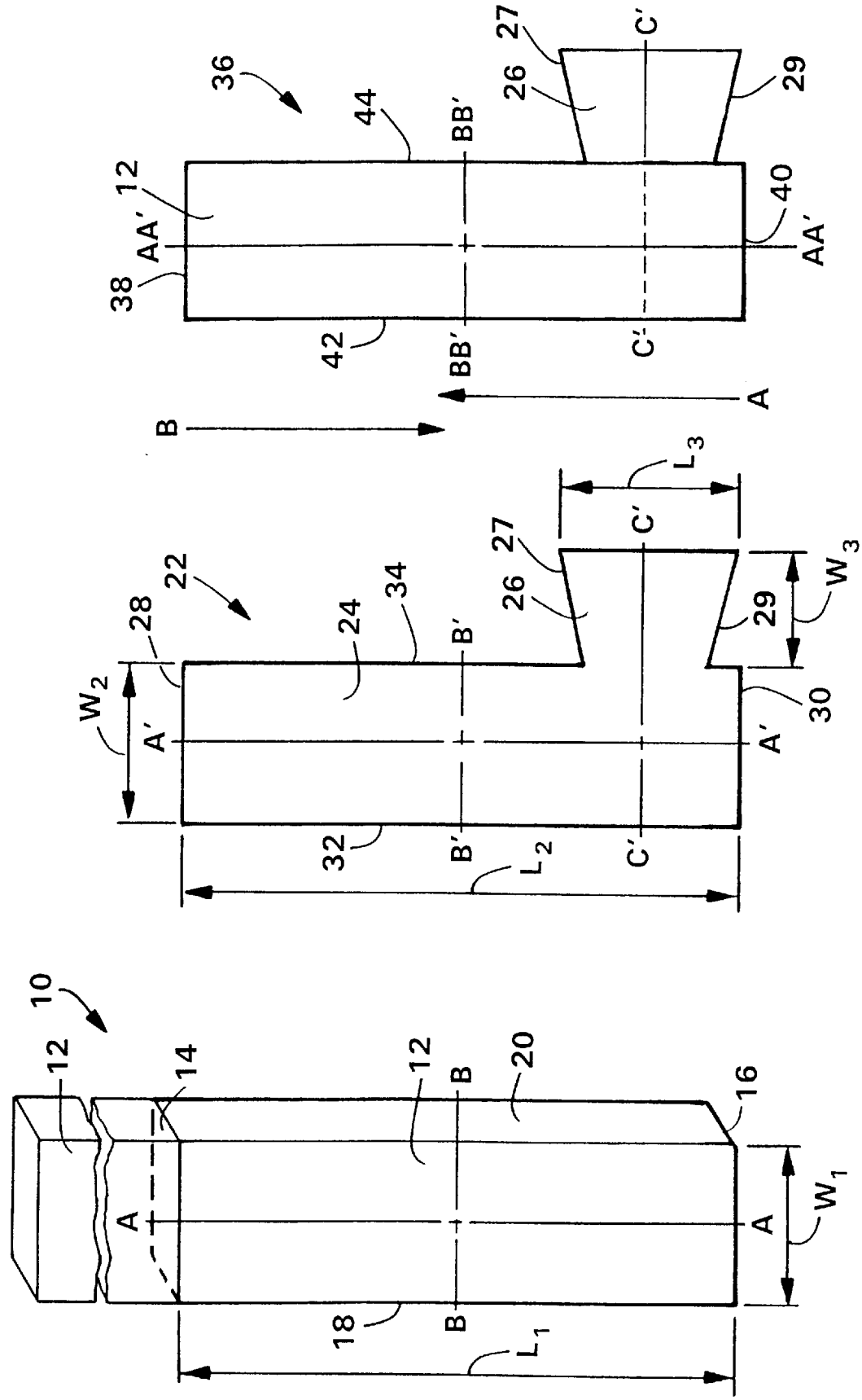

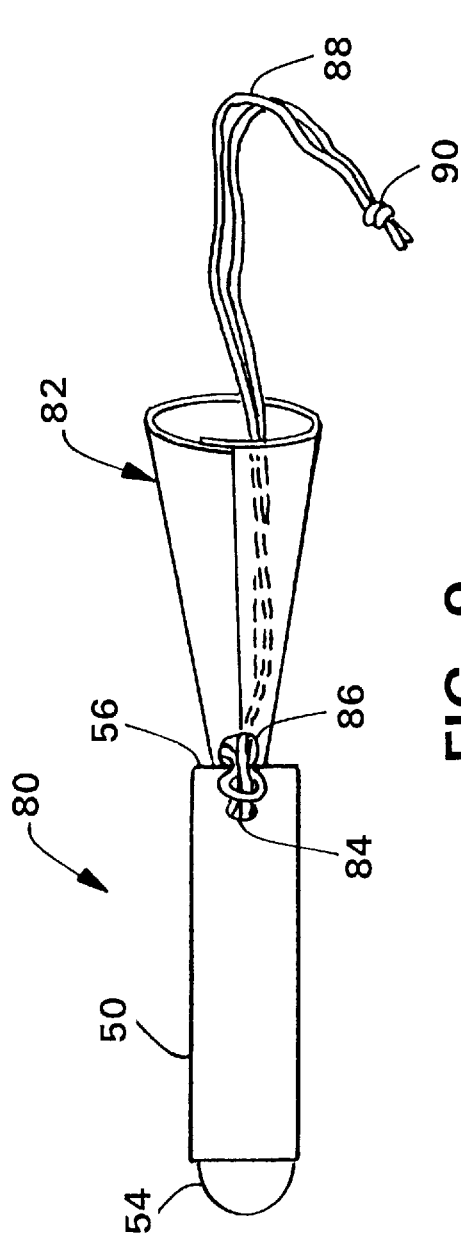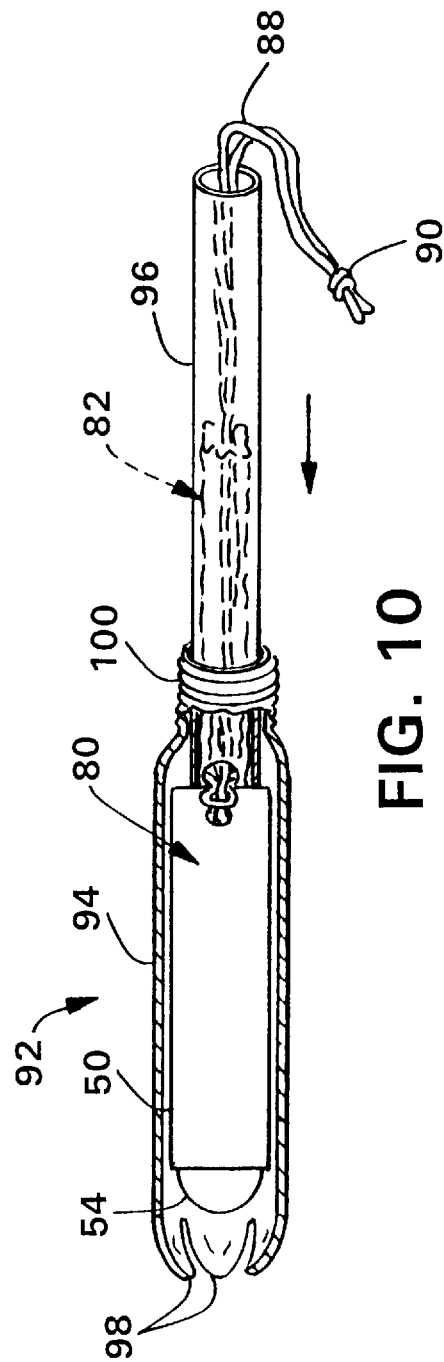

TAMPON HAVING A PROTECTIVE FINGER SHEATH AND A METHOD OF FORMING

This application is a continuation-in-part of application Ser. No. 08/426,393, entitled "TAMPON HAVING A PROTECTIVE FINGER SHEATH AND A METHOD OF FORMING" and filed in the U.S. Patent and Trademark Office on Apr. 21, 1995 and now abandoned. The entirety of this application is hereby incorporated by reference.

FIELD OF THE INVENTION

This invention relates to a catamenial tampon having a protective finger sheath and a method of forming such a tampon. More particularly, this invention relates to a catamenial tampon designed to be worn by a female during her menstrual period to absorb menstrual fluid, blood, etc.

BACKGROUND OF THE INVENTION

Currently, there are two basic types of catamenial tampons used for feminine hygiene. The first type is a digital tampon which is designed to be inserted into a woman's vagina directly by the user's fingers. The second type is a tampon which is designed to be inserted with the aid of an applicator. Both types are usually made by folding or rolling a loosely associated strip of absorbent into a cylindrical shape referred to as a "softwind" and then radially and/or biaxially compressing the softwind into a pledget. The pledget may or may not include a cover. In both types of tampons, a withdrawal string is attached to the softwind either before or after compression. The withdrawal string facilitates removal of the tampon from the user's vagina after it has absorbed menstrual fluid, blood, etc.

It has been found that many women shy away from the digital style tampon because they can experience soiling of their fingers with body fluid while inserting a fresh tampon into their vagina. It has also been recognized that many women experience some difficulty in trying to located and grasp the withdrawal string when they are ready to remove the tampon from their vagina. It is common for the withdrawal string to curl up and adhere to the distal end of the tampon. When the user searches for the string with her fingers, she finds that it is hard to locate. Once the withdrawal string is found, the user finds that her fingers have been soiled and may not have access to a sink where she can wash up.

Another problem is that sometimes the withdrawal string becomes separated from the absorbent pledget during the removal process. The user is then forced to pinch the tampon between her fingers and physically remove it or seek medical assistance. In the former situation, it is difficult for her to avoid soiling her fingers on the tampon filled with menstrual fluid.

Now a tampon with a protective finger sheath and a method of forming the tampon have been invented to overcome these frustrating inconveniences.

SUMMARY OF THE INVENTION

Briefly, this invention relates to a tampon having a protective finger sheath and a method of forming the tampon. The tampon is constructed from an absorbent having a first end and a second end. An L-shaped cover having a leg, a foot and a central longitudinal axis is aligned with the absorbent such that the foot is aligned adjacent to the second end of the absorbent. Both the absorbent and the cover are rolled or wound up along the central longitudinal axis of the absorbent-cover combination into a cylindrically shaped softwind which is compressed into an absorbent pledget. The absorbent pledget has a predetermined diameter, an insertion end, a trailing end, and a flexible sheath which extends outward from the trailing end. The flexible sheath is sized to receive a user's finger and prevent soiling of the finger during insertion of the absorbent pledget into a body cavity. The flexible sheath also enables the absorbent pledget to be removed from the body cavity in a clean and easy manner.

The method of forming the tampon includes forming an absorbent ribbon having a predetermined width. Positioning the absorbent ribbon over a cover such that a portion of the cover extends beyond the width of the absorbent ribbon. The absorbent ribbon and the cover are then cut to a desired length if they already were not in the correct size. Both materials are then rolled or wound up into a cylindrically shaped softwind. The softwind is compressed into an absorbent pledget having an insertion end, a trailing end and a flexible sheath which extends outward from the trailing end.

The general object of this invention is to provide a catamenial tampon having a protective finger sheath and a method of forming the tampon. A more specific object of this invention is to provide a catamenial tampon having a cover integrally attached to the absorbent.

Another object of this invention is to provide a catamenial tampon which does not require a withdrawal string.

A further object of this invention is to provide a catamenial tampon having a visually distinctive appearance.

Still another object of this invention is to provide a catamenial tampon which prevents the user's finger from becoming soiled by body fluid during insertion and removal of the tampon into and out of her vagina.

Still further, an object of this invention is to provide a tampon with a flexible finger sheath which can collapse once the tampon is inserted into the vagina cavity so as to be unnoticeable to the wearer.

Other objects and advantages of the present invention will become more apparent to those skilled in the art in view of the following description and the accompanying drawings.

BRIEF DESCRIPTION OF THE DRAWINGS

FIG. 1 is a perspective view of an absorbent having a rectangular configuration.

FIG. 2 is a top view of a cover having an L-shaped configuration.

FIG. 3 is a top view of the absorbent overlaying the L-shaped cover.

FIG. 9 is a side view of a tampon having a protective finger sheath along with a withdrawal string.

FIG. 10 is a perspective view of a tampon shown in FIG. 7 positioned in a partially cutaway view of a tampon applicator.

DETAILED DESCRIPTION OF THE PREFERRED EMBODIMENT

Figure 4:
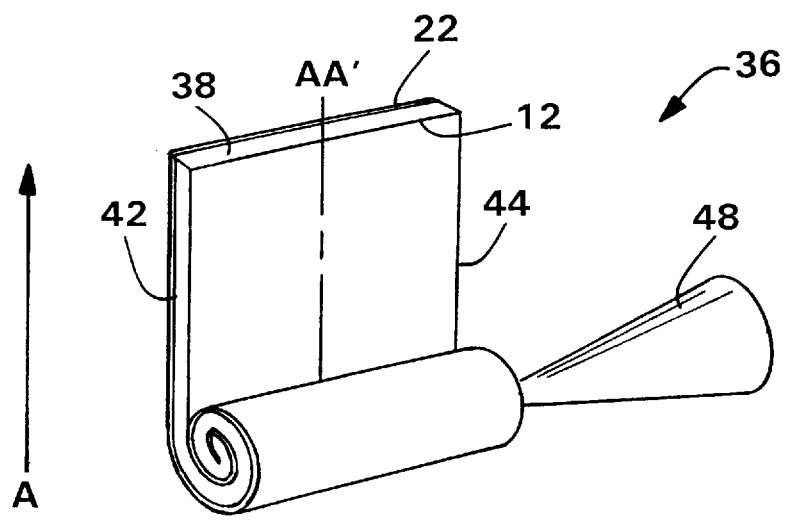
FIG. 4 is a top view of the absorbent and cover being rolled or wound up on itself to form a softwind having a flexible finger sheath.

Referring to FIG. 1, an elongated absorbent ribbon 10 is shown having a rectangular configuration. From this absorbent ribbon 10, one or more individual absorbent members 12 can be cut. Each absorbent member 12 has a predetermined length $L_1$, a width $W_1$, a central longitudinal axis A—A and a central transverse axis B—B. The central transverse axis B—B is aligned 90 degrees to the central longitudinal axis A—A. The absorbent member 12 has first and second spaced apart ends 14 and 16, respectively, and first and second longitudinal side edges 18 and 20, respectively, which are also spaced apart from one another. The first and second ends 14 and 16 are aligned approximately parallel to one another as are the longitudinal side edges 18 and 20. It should be noted that the length $L_1$ of the absorbent member 12 is longer in dimension than its width $W_1$.

The absorbent ribbon 10 can be made from natural or artificial fibers including polyester, cellulose, acetate, nylon, polypropylene, rayon, cotton or blends thereof. The absorbent ribbon 10 can also be a nonwoven, such as a bonded carded web, an airlayed web or a needle punched web. Such webs can be constructed of cotton and rayon fibers. A homogeneous blend of bleached cotton fibers and rayon fibers works well. The absorbent fibers can be formed by convolutely winding multiple fibers into a ribbon. Each absorbent member 12 cut from the absorbent ribbon 10 can have a length $L_1$ ranging from between about 4 to about 14 inches (about 102 mm to about 356mm), preferably from about 6 inches to about 8 inches (about 152 mm to about 203 mm), and most preferably, about 7 inches (about 178mm). The width $W_1$ of each absorbent member 12 can range from between about 1 inch to about 5 inches (about 25 mm to about 127 mm), preferably from about 2 inches to about 4 inches (about 51 mm to about 102 mm), most preferably, about 2.75 inches (about 70mm). The thickness of each absorbent member 12 can vary depending upon the diameter of the tampon one wishes to manufacture. A thickness of from between about 0.08 inches to about 0.28 inches (about 2mm to about 7mm) works well for a digital tampon.

Referring to FIG. 2, a liquid-permeable cover material 22 is shown having an L-shaped configuration with an upstanding leg portion 24 and a horizontally aligned foot portion 26. The cover 22 has a central longitudinal axis A'—A' and a central transverse axis B'—B'. The central transverse axis B'—B' is aligned 90 degrees to the central longitudinal axis A'—A'. The cover 22 has first and second spaced apart ends, 28 and 30 respectively, and first and second longitudinal side edges, 32 and 34 respectively, which are also spaced apart from one another. The first and second ends, 28 and 30, are aligned approximately parallel to one another as are the first and second longitudinal side edge, 32 and 34. The foot portion 26 of the cover 22 is divided in half by a transverse axis C'—C' which is spaced apart from the central transverse axis B'—B'.

The cover 22 can be constructed of a perforated or nonperforated nonwoven, from a thermoplastic film which has been perforated to make it liquid-permeable or from some other type of liquid-permeable material. The cover 22 can have a thickness of from between about 0.01 mm to about 1.0 mm, preferably less than about 0.5 mm, and most preferably, less than 0.3 mm. The thickness of the cover 22 should be less than about 50 percent of the thickness of the absorbent member 12. Preferably, the thickness of the cover 22 is less than about 10 percent of the thickness of the absorbent member 12, and more preferably, less than about 5 percent of the thickness of the absorbent member 12.

The cover 22 can be treated with an emollient, a lubricant, or a surfactant to give it certain qualities. An emollient can be used to make the cover 22 softer and less abrasive. A lubricant can be used to facilitate insertion of the tampon into a woman's vagina. A surfactant can be used to allow body fluid to penetrate the cover 22 or to make the cover 22 more hydrophilic, that is, to increase it's affinity for absorbing fluids. It is also possible to treat a portion of the cover 22 to make it hydrophobic so that it will shed fluid. For example, the foot portion 26 of the cover 22 could be treated to be hydrophobic while the leg portion 24 of the cover 22 could be treated to be hydrophilic.

The cover 22 can be constructed of natural or synthetic materials and should be easily penetrated by body fluid, such as menstrual fluid, blood, etc. Suitable materials include nonwovens, bonded carded webs of polyester, polypropylene, polyethylene, nylon or other heat-bondable fibers. Other polyolefins, such as copolymers of polypropylene and polyethylene, linear low density polyethylene, finely perforated thermoplastic films and net materials, also work well. A preferred material is spunbond which is manufactured and sold by Kimberly-Clark Corporation. Another material that also works well is a neck-bonded laminate manufactured by Kimberly-Clark Corporation. The neck-bonded laminate is constructed of an elastomeric film which is thermally laminated in an unstretched state between two spunbond facing sheets. One such neck-bonded laminate is commercially sold under the trademark KRATON. The neck-bonded laminate has sufficient strength as well as the ability to stretch in the cross direction instead of in the machine direction. Having a cover material that can stretch in only one direction is advantageous when forming the flexible sheath.

The cover 22 has an overall length $L_2$ which can be less than, equal to, or greater than the length $L_1$ of the absorbent member 12. The cover 22 also has two width dimensions, the first width $W_2$ corresponding to the width of the leg portion 24 while the second width $W_3$ corresponding to the width of the foot portion 26. In the L-shaped configuration, the width $W_2$ can be less than, equal to, or greater than the width $W_1$ of the absorbent member 12 while the width $W_3$ of the foot portion 26 can be less than, equal to or greater than the width $W_2$. Preferably, the width $W_2$ of the leg portion 24 will be less than or equal to the width $W_1$ of the absorbent member 12 and the width $W_3$ of the foot portion 26 will be less than the width $W_2$.

Still referring to FIG. 2, the foot portion 26 of the cover 22 is depicted as having a trapezoid profile with a first end 27 and a second end 29. Although this design forms a preferred sheath, a square, a rectangle or other type of configuration is acceptable. The length $L_3$ of the foot portion 26 can extend a distance from between about 20 to about 75 percent of the overall length $L_2$ of the cover 22. Preferably, $L_3$ will range from between about 20 to about 50 percent of the length $L_2$ of the cover 22. It has been found that by making the length $L_3$ only a fraction of the total length $L_2$ of the cover 22, that less cover material is needed and this can reduce the overall cost required to produce the tampon. A second benefit of making $L_3$ less than about 50 percent of the overall length $L_2$ of the cover 22 is that it will be easier for a woman to insert her finger into the flexible sheath which is formed.

Referring to FIG. 3, an individual absorbent member 12 which has been cut from the absorbent ribbon 10 is positioned on top of and is aligned with the cover 22 to produce an absorbent-cover combination 36. In the absorbent-cover combination 36, the absorbent ribbon 12 and the cover 22 are depicted as having the same length, $L_1$ is equal to $L_2$ and the width $W_1$ of the absorbent member 12 is equal to the width $W_2$ of the leg portion 24 of the cover 22. The absorbent-cover combination 36 has first and second spaced apart end, 38 and 40 respectively, and first and second longitudinal side edges, 42 and 44 respectively. The first and second ends 38 and 40 are aligned parallel to one another as are the first and second longitudinal side edges 42 and 44. The absorbent-cover combination 36 has a central longitudinal axis AA'—AA' and a central transverse axis BB'—BB'. The central transverse axis BB'—BB' is aligned 90 degrees to the central longitudinal axis AA'—AA'. In the absorbent-cover combination 36, the central transverse axis BB'—BB' is spaced apart from the transverse axis C'—C' which dissects the foot portion 26 of the cover 22.

It should be noted that the absorbent member 12 can be longitudinally and/or transversely offset from the cover 22, if desired. The particular alignment one uses will depend upon the final pledget design. When at least a portion of the absorbent member 12 extends over at least one of the longitudinal side edges 32 or 34 of the cover 22, it eliminates the necessity of having to cut the absorbent member 12 and the cover 22 to the same width. This can be advantageous for some tampon design.

Figure 5:
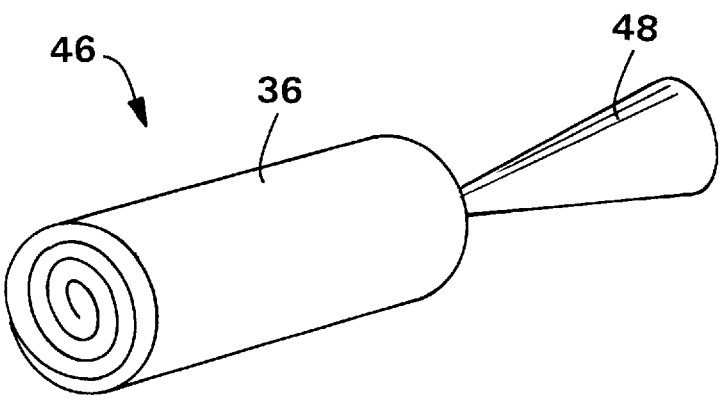
FIG. 5 is a top view of the rolled up softwind.

Referring to FIGS. 4 and 5, the absorbent member 12 is overlaid on to the cover 22 and both are rolled or wound up into the absorbent-cover combination 36. If it is necessary to cut the absorbent member 12 and or the cover 22 into a desired length, this should be done before the two materials are rolled up. When the absorbent member 12 and the cover 22 are rolled or wound up, such as by radially winding both material together along the central longitudinal axis AA'—AA', a cylindrical shape is formed which is known in the art as a "softwind" 46. It should be noted that the absorbent member 12 and the cover 22 can be rolled or wound up by starting from either the first end 38 or from the second end 40. However, the finished shape of a flexible finger sheath 48 which if formed by this operation will be different depending upon which end one starts to wind up the materials. The softwind 46 refers to a tightly rolled or wound absorbent member 12 having a generally cylindrical shape which has not yet been compressed. The softwind 46 may or may not include a cover 22. After the softwind 46 has been constructed, it is normally compressed into a pledget 50, which is shown in FIG. 6.

The diameter of the softwind 46 can vary depending upon the starting thickness of the absorbent member 12, the thickness of the cover 22, the degree to which the absorbent member 12 and cover 22 have been rolled or wound up, the desired diameter of the finished pledget 50, etc. U.S. Pat. No. 4,951,368 issued Aug. 28, 1990 to Heinen, and assigned to Kimberly-Clark Corporation, teaches an apparatus for compressing an absorbent into a tampon.

Figure 6:
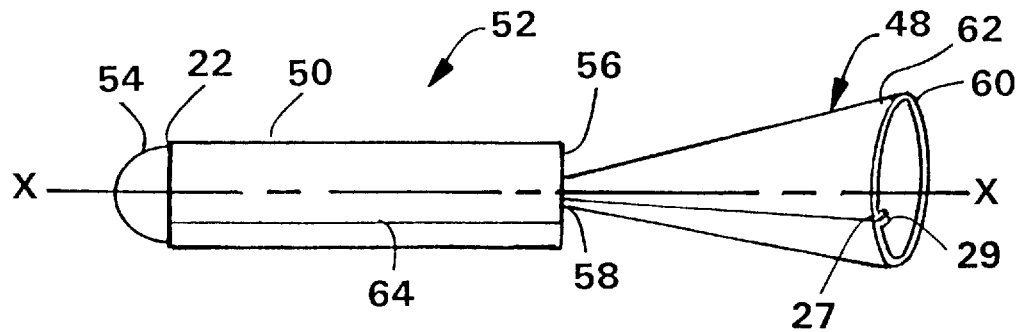
FIG. 6 is a side view of a compressed pledget rolled up in direction "A" as indicated in FIG. 3 whereby the flexible sheath acquires a conical appearance.

Referring now to FIG. 6, a catamenial tampon 52 is shown which is formed by rolling the absorbent-cover combination 36 in the direction indicated as "A" in FIG. 3, starting from the second end 40 and proceeding toward the first end 38. After the softwind 46 is formed, it is compressed in to a pledget 50. The tampon 52 includes the flexible finger sheath 48 having a conical configuration which is integrally secured to the absorbent pledget 50. It is critical to obtaining the conical sheath configuration that the absorbent-cover combination 36 be rolled or wound starting from the second end 40. By "rolling or winding" is meant that the absorbent-cover combination 36 is rolled up upon itself along the central longitudinal axis AA'—AA'. That is, the absorbent-cover combination 36 is rolled up perpendicular to the central longitudinal axis AA'—AA'.

The flexible sheath 48 extends perpendicularly outward from the diameter of the absorbent pledget 50 for a distance equal to at least half of the length of the absorbent pledget 50.

The absorbent member 12 and the cover 22 will be bonded together by heat, pressure or a combination of heat and pressure during the compression step and therefore cannot be separated without destroying the tampon 52. The pledget 50 has an insertion end 54 spaced apart from a trailing end 56. The insertion end 54 is not covered by the cover 22 so as to allow for a faster absorption of body fluid once the tampon 52 is placed inside a woman's vagina. The insertion end 54 can be rounded or pointed to form an angled nose, for example, a semi-spherical shaped nose, which will facilitate insertion of the tampon 52 into a woman's vagina. Covering and extending longitudinally outward from the trailing end 56 of the pledget 50 is the flexible finger sheath 48. The flexible finger sheath 48 is an extension of the cover 22 and forms a hollow skirt which is sized and shaped to receive a user's finger. When the absorbent-cover combination 36 is rolled up starting from the second end 40, the finger sheath 48 will acquire a conical configuration as depicted in FIG. 6.

The portion of the cover 22 surrounding the pledget 50 is integral with the portion of the cover 22 which forms the flexible sheath 48. The cover 22 encloses the trailing end 56 of the pledget 50 and is gathered at a point 58 which is located adjacent to the longitudinal axis X—X of the tampon 52. This point 58 is located approximately at the apex of the flexible sheath 48. The flexible sheath 48 has a flexible wall 60 which angles radially outward as it moves away from the trailing end 56 of the pledget 50. This flexible wall 60 forms a cone 62 having an internal diameter which is large enough to receive and enclose a portion of a user's finger.

When the flexible finger sheath 48 is rolled or wound up in direction "A", as depicted in FIG. 4, such that the second end 29 becomes the inside edge of the cone 62 and the first end 27 becomes the outside edge of the cone 62. The two ends 27 and 29 form a circular arc which spans at least 360 degrees such that the first end 27 at least abuts the second end 29. Preferably, the first end 27 will overlap the second end 29 at least once. The overlap can be obtained by having the flexible wall 60 span an arc of greater than 360 degrees. It should be noted that the flexible wall 60 can span an arc of up to about 1,080 degrees. Three concentric windings of the wall 60 will provide an arc of 1,080 degrees. The exact amount of overlap will depend upon the length of the cover 22 and how it is aligned relative to the absorbent member 12. It is possible to have more than three complete circular arcs if desired. However, the presence of multiple 360 degree windings could interfere with the insertion of a user's finger into the flexible sheath 48. When the cover 22 is made of a very thin material, multiple wrappings can decrease the ease at which a user can insert her finger into the flexible sheath 48.

The overlap of the ends 27 and 29 of the wall 60 assures that the circumference of the user's finger, which will be positioned in the flexible sheath 48, will be completely protected from being soiled by body fluid. If it wasn't for the flexible sheath 48, a woman could encounter menstrual fluid, blood, etc. during the insertion process which could soil her fingers as she inserts the tampon 52.

The flexible sheath 48 has a conical profile and should have an outside diameter at its free end which is larger than the outside diameter of the pledget 50. This size difference will facilitate insertion of a woman's finger into the flexible sheath 48. It should also be mentioned that the flexible sheath 48 is very flexible and the wall 60 will collapse upon itself when the tampon 52 is inserted into the woman's vagina. The collapse of the flexible sheath 48 is beneficial in that it cannot be detected by the wearer and therefore provides for a more comfortable product. The thinnest of the cover 22 contributes to the flexibility of the sheath 48 and allows it to collapse once the woman's finger is withdrawn.

It should be mentioned that it is possible to chemically treat only a certain portion of the cover 22 or to perforate only a given area of the cover 22, if desired. For example, an emollient or a surfactant could be applied to only that portion of the cover 22 which surrounds the pledget 50. Furthermore, it is not necessary to perforate the portion of the cover 14 which forms the sheath 28 because one does not want body fluid to penetrate through the flexible sheath 48. It is also not desirable to lubricate the portion of the cover 22 which forms the flexible sheath 48 because one does not want the user's finger to slip out of the flexible sheath 48 during the insertion process. Likewise, it is not necessary to treat the flexible sheath 48 with a hydrophilic surfactant. However, the flexible sheath 48 could be treated to prevent or inhibit fluid penetration with a material such as wax.

Referring again to FIG. 6, the cover 22 can be secured to the absorbent member 12 over the entire length of the pledget 50 during the compression step by a seam 64. In addition, the cover 22 can be secured to itself over at least a portion of the length of the flexible sheath 48 by an extension of the seam 64. The seam 64 will ensure that the first end 27 does not move away from abutting or overlapping the second end 29. The seam 64 can be formed by applying heat, pressure, or the combination of heat and pressure. Furthermore, the seam 64 can be formed by using an adhesive, by sewing, by ultrasonic bonding, or by any other means known to those skilled in the art. The seam 64 can be intermittent or continuous, depending on the particular manufacturing process employed, and does not have to extend over the total width $W_3$ of the foot portion of the cover 22.

It should also be noted that along the length of the flexible sheath 48, the seam 64 can be formed by a different process than that used to form the seam 64 along the length of the pledget 50. For example, the seam 64 can be formed over the length of the pledget 50 by using heat and pressure to bond the cover 22 to the absorbent member 12 while an ultrasonic bond can be used to form the seam 64 over the length of the flexible sheath 48.

Figure 7:
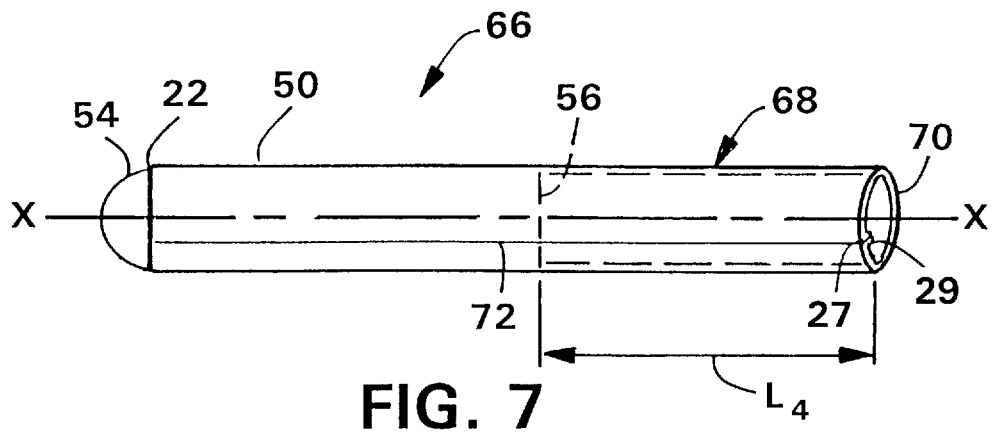
FIG. 7 is a side view of a compressed pledget rolled up in direction "B" as indicated in FIG. 3 whereby the flexible sheath acquires a tubular appearance.

Referring to FIG. 7, a catamenial tampon 66 is shown which is formed by forming a softwind by rolling or winding up the absorbent member 12 and cover 22 in the direction indicated as "B" in FIG. 3. The softwind is then compressed into a pledget 50. The tampon 66 includes a flexible sheath 68 integrally secured to the absorbent pledget 50. The sheath 68 has a tubular configuration instead of the conical configuration shown in FIG. 6. The pledget 50 is identical to that described above and includes the insertion end 54 spaced apart from the trailing end 56. The difference in FIG. 7 is that the cover 22 extends longitudinally outward from the outer circumference of the pledget 50 to form a flexible sheath 68 having a hollow, tubular configuration. The outside diameter of the tubular sheath 68 is essentially constant and equal to the outside diameter of the pledget 50. The inside diameter of the tubular shaped sheath 68 should be of a sufficient size to allow the insertion of a woman's finger or thumb. The tubular configuration of the flexible sheath 68 is an option to the conical configuration of the flexible sheath 48 shown in FIG. 6. However, both of the flexible sheaths 48 and 68 functions in a similar fashion.

Referring again to FIG. 7, the tubular sheath 68 has a flexible wall 70 which spans an arc of at least 360 degrees. The ends of the wall 70 can be secured together by a seam 72. The seam 72 can extend along the length of the pledget 50 as well as along the length of the flexible sheath 68 to ensure that the first end 27 or the outer end of the foot portion of the cover 22 does not move away from abutting or overlapping the second end 29 or the inner end of the foot portion of the cover 22. The seam 72 can be formed as stated above. The flexible sheath 68 also has a length $L_4$ in its finished condition which is equal to the initial starting width $W_3$, which is shown in FIG. 2. This length should be long enough to enclose one of the user's fingers or thumb, preferably the index or middle finger, and extend pass the fingernail and up to the first knuckle. Preferably, the flexible sheath 68 has a sufficient length to approach and possible cover the second knuckle.

It should be noted that a benefit of the conical shaped finger sheath 48 is that it more easily allows the user's finger to enter and exit the opening formed in the flexible sheath 48. Some consumers may even experience better control of the pledget 50 by using the conical shaped finger sheath 48. The finger sheath 48 and 68 of the present invention also enables a manufacture to make the product using less material than if a rectangular sheet of cover material was used. This cost saving could be passed on to the ultimate consumer. Less material for the finger sheath 48 or 68 further means that it will be more comfortable to wear since the user will not notice its presence. Another advantage of the present finger sheath 48 or 68 is that it is constructed such that it is integrally formed with the absorbent member 12 so that the two members can not be separated. This assures that the finger sheath 48 or 68 will always be available as a withdrawal means for assisting in removing the tampon 52 or 66 from the woman's vagina. The ultimate consumer does not have to be concerned with a withdrawal string which might break or pull away from the absorbent member 12.

Figure 8:
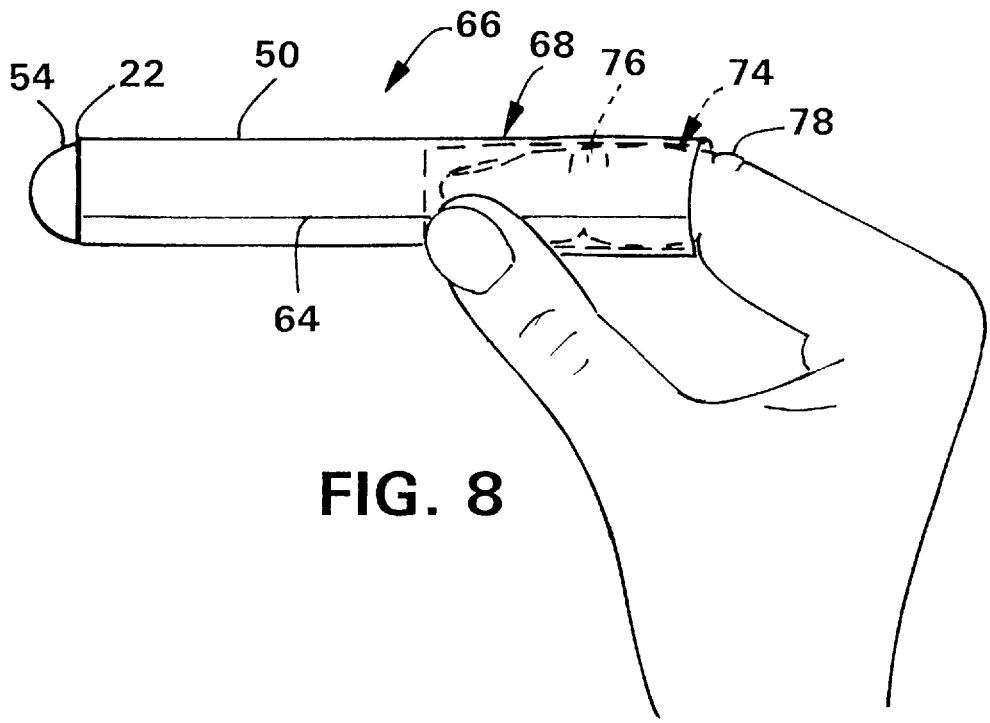
FIG. 8 is a schematic view depicting a woman's index finger positioned in the protective flexible sheath and ready to place the tampon into her vagina.

Referring to FIG. 8, a schematic view is shown depicting a woman's index finger 74 positioned inside the tubular shaped sheath 68 of the tampon 66. The flexible sheath 68 should enclose the first finger joint or knuckle 76 and extend up to, or at least adjacent to, the second finger joint or knuckle 78. The flexible sheath 68 should extend longitudinally outward from the cylindrically shaped pledget 50 for a distance equal to at least half the length of the cylindrically shaped pledget 50. For example, the flexible sheath 68 can have a length of at least 0.5 inches (12.7 mm), preferably, at least 1.0 inches (25.4 mm), and most preferably, at least 1.5 inches (38.1 mm). This distance will vary for each woman and therefore the preferred length will depend on the preference of each manufacturer. Another way of constructing the tampon 66 is to make the length of the flexible sheath 68 approximately equal to the length of the pledget 50.

It should be realized that even though the index or middle fingers are the ones most likely to be used by a woman to insert the tampon 52 or 66, some women may prefer to use a different finger or even the thumb. Any finger, including the thumb, should be accommodated by the inner opening of the flexible sheath 48 or 68. As explained above, after the tampon 52 or 66 is inserted into a woman's vagina, the flexible sheath 48 or 68 will collapse upon itself and be virtually unnoticeable by the wearer.

It should be noted that the user can use her thumb to squeeze the flexible sheath 48 or 68 against the tip of the index finger 74 so as to control the orientation of the pledget 50 as it is initially positioned at the opening of her vagina. Some women may find it desirable to position the tip of the thumb at the base of the pledget 50 to gain greater control. Likewise, some women may find the insertion process to be easier if they place their middle finger in the flexible sheath 48 or 68 and use and use both their thumb and ring finger on the outside of the flexible sheath 48 or 68. The thumb and ring finger would be withdrawn after the pledget 50 is aligned with the opening of the vagina and only the middle finger would be used to insert the pledget 50 into the vagina. It is also possible for a user to twist the flexible sheath 48 or 68 once her finger is inserted into it, so as to obtain greater control of the tampon 52 or 66. The flexible sheath 48 or 68 should be sized and configured to accommodate these various styles of insertion.

Referring to FIG. 9, an alternative embodiment of the tampon 80 is shown having a pledget 50 with an integrally attached flexible finger sheath 82. The flexible sheath 82 has a conical configuration and is obtained by rolling or winding up the absorbent member 12 and the cover 22 as taught above with reference to FIGS. 4–6. In this embodiment, the pledget 50 has an opening 84 formed therein approximate the trailing end 56 and the flexible sheath 82 has an opening 86 located adjacent to the trailing end 56. A withdrawal string 88 passes through the opening 84 formed in the pledget 50 and is looped upon itself. The withdrawal string 88 then passes through the opening 86 formed in the flexible sheath 82 so that it can be routed through the interior of the flexible sheath 82. The withdrawal string 88 extends along the interior length of the flexible sheath 82 and out through the enlarged open end thereof. The free ends of the withdrawal string 88 terminate outside of the flexible sheath 82 where they are secured together by a knot 90. The knot 90 insures that the withdrawal string 88 cannot be separated from the pledget 50. The withdrawal string 88 can contain a wax coating to prevent it from absorbing body fluid. The flexible sheath 82 shelters the withdrawal string 88 from contacting the inside walls of the woman's vagina and thereby serves to keep the withdrawal string 88 clean and dry so that it can be used to withdraw the tampon 80 without soiling the fingers of the user. The flexible sheath 82 also functions to provide a backup means for withdrawing the pledget 50 should the withdrawal string 88 break.

Referring to FIG. 10 the tampon 80 is shown positioned within a tampon applicator 92. One type of tampon applicator is taught in U.S. Pat. No. 5,158,535 issued to Paul et al. on Oct. 27,1992, and is assigned to the present assignee. The tampon applicator 92 is constructed of an outer tube 94 and an inner tube 96. The outer tube 94 is sized and configured to house the pledget 50 and includes a plurality of flexible petals 98 formed on the forward or expulsion end. The petals 98 are designed to flex or bend outward to provide an opening through which the pledget 50 can be ejected from the outer tube 94 at the appropriate time. The opposite end of the outer tube 94 narrows into a fingergrip portion 100 which provides a surface which can accommodate the users thumb and middle finger so that the outer tube 94 can be properly positioned in the user's vagina. The inner tube 96 is a hollow member which is telescopically movable within the fingergrip portion 100 of the outer tube 94. When the inner tube 96 is pushed forward into the outer tube by the user's index finger, it will contact the pledget 50 and expel it through the opening formed when the petals 98 separate. As this occurs, the flexible sheath 82 and the withdrawal string 88 pass through the hollow inner and outer tubes, 96 and 94 respectively. The tampon applicator 92 can then be discarded.

It should also be mentioned that the pledget 50 can have an opening formed in its trailing end 56 which is designed to receive a stick. The stick serves as an applicator and can be removed once the tampon 80 is positioned in the user's vagina. U.S. Pat. No. 3,683,912 issued to Olson et al. and assigned to the present assignee teaches such a stick tampon.

Figure 11:
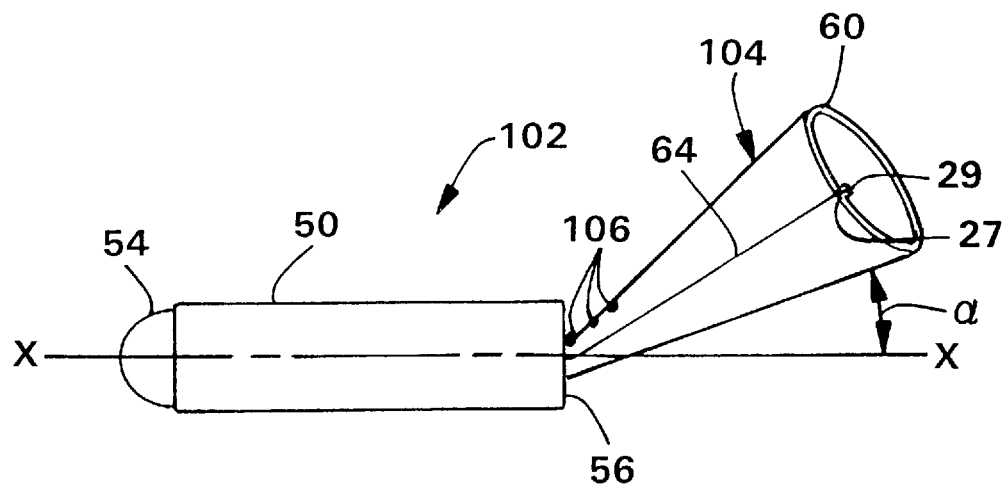
FIG. 11 is a side view of an alternative embodiment wherein the flexible sheath has a conical appearance and is angularly offset from the pledget.

Referring to FIG. 11, an alternative embodiment of a tampon 102 is shown wherein a flexible sheath 104 is offset from the longitudinal axis X—X by an angle alpha (a). The angular offset can facilitate positioning the tampon 102 into a woman's vagina. This angular offset can be obtained a number different ways. One way is to apply one or more spots of adhesive 106, such as a construction glue, to bond the flexible sheath 104 to the trailing end 56 of the pledget 50. The adhesive 106 can be applied as one or more dots, or as a continuous line or seam, to that portion of the flexible sheath 104 which is needed to hold it at a desired angle. The angle can vary from about 10 degrees to about 75 degrees, with an angle of between about 20 degrees to about 45 degrees working the best. It should be noted that the adhesive 106 can be spaced apart from the seam 64 which forms the flexible sheath 104, as shown, or the adhesive 106 can be aligned with and applied along the seam 64.

Figure 12:
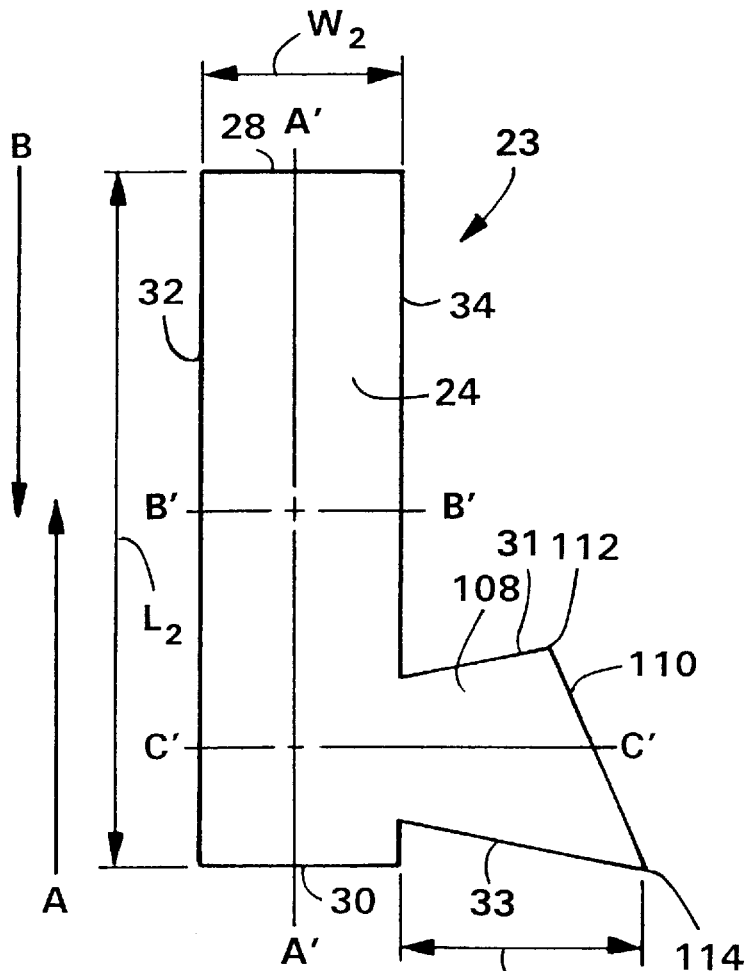
FIG. 12 is a top view of a cover having a modified L-shaped configuration to form a conical sheath that is offset at an angle from the pledget.

Referring to FIG. 12, a second way to obtain the flexible sheath 104 at an angular orientation to the pledget 50, as is shown in FIG. 11, is to cut a cover 23 into a unique shape. The cover 23 is cut to a shape such that it has a rectangular shaped leg 24 with an odd shaped foot 108 extending outward therefrom. The leg 24 has a length $L_2$ and a width $W_2$. The foot 108 has a width $W_6$. The foot 108 differs from the foot 26, shown in FIG. 2, in that it has an edge 110 formed by a line joining points 112 and 114. The edge 110 is formed at an angle to the longitudinal side edge 34 of the cover 23 so that when the cover 23 is rolled up, the flexible sheath 104 will fold or bend at the trailing end 56 of the pledget 50 and exhibit the angular offset. The offset can be enhanced by the addition of the seam 64 which secures a first end and a second end 31 and 33 respectively, of the foot 108 together. In addition, it should be mentioned that one or more spots of adhesive 106 can also be utilized, as shown in FIG. 11, to maintain the desired angular offset.

METHOD

Figure 13:
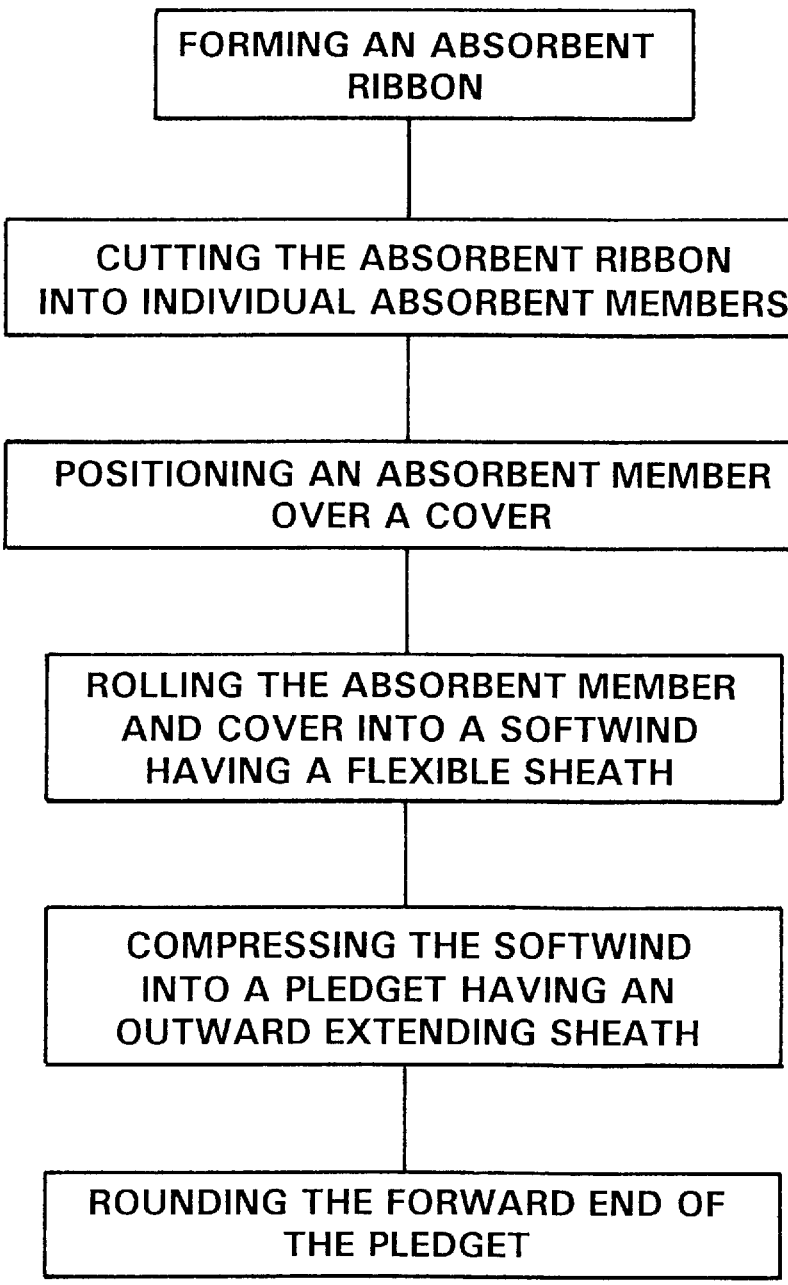
FIG. 13 is a flow diagram depicting a method of forming the tampon with a protective finger sheath.

Referring to FIG. 13, a flow diagram is shown depicting a method of forming the catamenial tampon having a protective finger sheath 48, 68, 82 or 104, although the method will only be specifically described with regard to the tampon having sheath 48. The method includes forming an elongated absorbent ribbon 10 which can be cut into individual absorbent members 12. Each absorbent member 12 has first and second spaced apart ends, 14 and 16 respectively, and first and second longitudinal side edges, 18 and 20 respectively. Each absorbent member 12 also has a predetermined length $L_1$, a predetermined width $W_1$, and a desired thickness. The length L, is longer than the width W, therefore, each of the longitudinal side edges, 18 and 20 respectively, is of a greater dimension than the ends, 14 and 16 respectively. The absorbent member 12 is positioned on or over an L-shaped cover 22 having a leg 24 and a foot 26. The cover 22 can be an apertured thermoplastic film which is liquid permeable. The absorbent member 12 is positioned on the cover 22 such that at least a portion of the cover 22 extends beyond at least one of the longitudinal edges 18 or 20 of the absorbent member 12. Preferably, the foot portion 26 of the cover 22 will extend beyond one of the longitudinal side edges of the absorbent member 12. The foot 26 has a length which extends a distance of at least 20% along the length of the leg 24. Another way of stating this configuration is to say that the L-shaped cover 22 has a total width ($W_2+W_3$) which is greater than the width $W_1$ of the absorbent member 12.

The absorbent member 12 and the L-shaped cover 22 are then rolled or wound up into a cylindrical softwind 46 having a desired diameter. The softwind 46 has a portion of the L-shaped cover 22 extending longitudinally outward from the end of the softwind 46 which forms an integral flexible finger sheath 48. The flexible sheath 48 includes a wall 60 which is formed into a tubular or conical configuration. The exact configuration depends upon which end of the absorbent-cover combination 36 is first rolled up from. When the L-shaped cover 22 is rolled up from the second end 40, a flexible sheath 48 is formed having a conical configuration with a hollow interior. When the L-shaped cover 22 is rolled up from the first end 38, a flexible sheath 68 is formed having a tubular configuration with a hollow interior. Preferably, the wall 60 of the flexible sheath 48 spans an arc of at least 360 degrees and the arc is circular in configuration. After the softwind 46 is formed, it is radially compressed into a pledget 50 having an insertion end 54 and a trailing end 56 with the flexible sheath 48 extending outward from the trailing end 56. The flexible sheath 48 forms an integrally secured protective finger sheath which cannot be separated from the pledget 50. Lastly, the insertion end 54 of the pledget 50 can be rounded to facilitate insertion of the tampon 52 into a woman's vagina.

It should be noted that the last step of the above described method can be eliminated if desired. It should also be noted that the sequence of some of the steps may be altered depending upon the equipment used to manufacture the tampon 52.

While the invention has been described in conjunction with several specific embodiments, it is to be understood that many alternatives, modifications and variations will be apparent to those skilled in the art in light of the a foregoing description. Accordingly, this invention is intended to embrace all such alternatives, modifications and variations which fall within the spirit and scope of the appended claims.

I claim:

1. A tampon comprising:
   a) an absorbent having first and second ends and a rectangular configuration; and
   b) a cover having an L-shaped configuration including a leg and a foot, said leg having a central longitudinal axis, said cover being aligned with said absorbent such that said foot is aligned adjacent to second end of said absorbent and both said cover and said absorbent are rolled up along said central longitudinal axis into a cylindrically-shaped softwind which is compressed into an absorbent pledget, said absorbent pledget having a predetermined diameter, an insertion end and a trailing end, and a flexible sheath defined by said foot of said cover extending outward from said trailing end, said flexible sheath sized to receive a user's finger and prevent soiling of the finger during insertion of said absorbent pledget into a body cavity, and said flexible sheath providing means for removing said absorbent pledget from the body cavity.

2. The tampon of claim 1 wherein said flexible sheath extends longitudinally outward from said trailing end of said absorbent pledget.

3. The tampon of claim 1 wherein said flexible sheath is capable of collapsing upon itself once said absorbent pledget is inserted into the body cavity and the user's finger is removed therefrom.

4. The tampon of claim 1 wherein said cover is an apertured thermoplastic film which is integrally secured to said absorbent pledget.

5. The tampon of claim 1 wherein said absorbent pledget has a length and said flexible sheath extends perpendicularly outward from the diameter of said absorbent pledget for a distance equal to at least half the length of said absorbent pledget.

6. The tampon of claim 3 wherein said flexible sheath extends longitudinally outward from said trailing end of said absorbent pledget for a distance of at least 1 inch.

7. The tampon of claim 1 wherein said flexible sheath has a tubular configuration.

8. The tampon of claim 1 wherein said flexible sheath has a conical configuration.

9. The tampon of claim 1 wherein a withdrawal string is secured to said absorbent pledget and extends outward through said flexible sheath.

10. A tampon comprising:
    a) an absorbent having a first end and a second end and a rectangular configuration; and
    b) a cover having an L-shaped configuration including a leg and a foot, said leg having a central longitudinal axis, said cover being aligned with said absorbent such that said foot is aligned adjacent to said second end of said absorbent and both said cover and said absorbent are wound up along said central longitudinal axis into a cylindrically shaped softwind which is compressed into an absorbent pledget, said absorbent pledget having a predetermined diameter, an insertion end and a spaced apart trailing end, and a flexible sheath defined by said foot of said cover extending longitudinally outward from said trailing end, said flexible sheath sized to receive a user's finger and prevent soiling of the finger during insertion of said absorbent pledget into a body cavity, and said flexible sheath providing means for removing said absorbent pledget from the body cavity.

11. The tampon of claim 10 wherein said flexible sheath has an interior and said flexible sheath contains an opening located adjacent to said trailing end of said pledget through which a withdrawal string attached to said pledget can pass and be routed through said interior of said flexible sheath.

12. The tampon of claim 10 wherein said pledget and flexible sheath are positioned in a tampon applicator, said applicator for containing said pledget and said flexible sheath prior to insertion of said pledget into the body cavity.

13. The tampon of claim 10 wherein said flexible sheath has a conical configuration which spans an arc of at least 360 degrees.

14. The tampon of claim 10 wherein said flexible sheath is offset from said central longitudinal axis by an angle alpha of from between about 10 degrees to about 75 degrees.

15. A catamenial tampon comprising:
a) an absorbent having a first end and a second end and a rectangular configuration; and
b) a cover having an L-shaped configuration including a leg and a foot, said leg having a central longitudinal axis, said cover being aligned with said absorbent such that said foot is aligned adjacent to said second end of said absorbent and both said cover and said absorbent are rolled up along said central longitudinal axis into a cylindrically shaped softwind which is compressed into an absorbent pledget, said absorbent pledget having a predetermined diameter, an insertion end and a trailing end, and a flexible sheath defined by said foot of said cover extending longitudinally outward from said trailing end, said flexible sheath spanning an arc of at least 360 degrees and being sized to receive a user's finger and prevent soiling of the finger during insertion of said absorbent pledget into a body cavity, and said flexible sheath providing means for removing said absorbent pledget from the body cavity.

16. The tampon of claim 15 wherein said cover at least partially encloses said absorbent and forms said flexible sheath which extends beyond said trailing end.

17. The tampon of claim 15 wherein said cover is an apertured thermoplastic film which is liquid permeable.

18. The tampon of claim 15 wherein said absorbent has a predetermined thickness and said cover has a thickness which is less than about 5 percent of the thickness of said absorbent.

19. A method of forming a tampon comprising:
a) forming an absorbent ribbon having a rectangular configuration;
b) cutting said absorbent ribbon into individual absorbent members;
c) positioning one of said absorbent members on a cover having an L-shaped configuration including a foot;
d) rolling both said absorbent member and said cover up into a cylindrically shaped softwind, said softwind having a flexible sheath defined by said foot of said cover extending outward therefrom; and
e) compressing said softwind into a pledget having an insertion end and a trailing end with said flexible sheath extending outward from said trailing end.

20. The method of claim 19 wherein said absorbent member has first and second ends and said cover has a leg and a foot, said leg having a length and said foot having a length which extends a distance of at least about twenty percent along the length of said leg, said absorbent member being positioned over said cover such that said second end of said absorbent member coincides with said foot and both said absorbent member and said cover are rolled up starting from said second end to form said flexible sheath, and said flexible sheath has a conical configuration.

21. The method of claim 20 wherein both said absorbent member and said cover are rolled up starting from said first end to form said flexible sheath and said flexible sheath has a tubular configuration.

22. A method of forming a tampon comprising:
a) forming an absorbent member having a predetermined width and a rectangular configuration;
b) positioning said absorbent member on a cover having an L-shaped configuration including a foot at least a portion of said cover having a width greater than the width of said absorbent member;
c) rolling both said absorbent member and said cover into a cylindrical softwind such that a portion of said cover extends longitudinally outward from said softwind and forms a flexible sheath, said sheath spanning an arc of at least 360 degrees;
d) compressing said softwind into a pledget having an insertion end and a trailing end with said flexible sheath defined by said foot of said cover extending outward from said trailing end; and
e) rounding said insertion end of said pledget to facilitate insertion of said pledget into a body cavity.

23. The method of claim 22 wherein said absorbent member and said L-shaped cover are rolled such that said flexible sheath acquires a conical configuration having an apex positioned adjacent to said trailing end of said pledget.

24. A method of forming a catamenial tampon comprising:
a) forming an absorbent ribbon having a rectangular configuration;
b) cutting said absorbent ribbon into individual absorbent members, each absorbent member having first and second ends and first and second longitudinal edges, and each of said longitudinal edges being of greater dimension than said ends;
c) positioning an absorbent member on a cover having an L-shaped configuration, said cover having a leg and a foot, said absorbent member and said cover being aligned such that a portion of said cover extends beyond one of said longitudinal edges of said absorbent member;
d) rolling said absorbent member and said cover in a longitudinal direction into a cylindrical softwind wherein said foot extends outward from said softwind and forms a flexible sheath; and
e) compressing said softwind into a pledget having an integrally secured protective finger sheath defined by said flexible sheath.

25. The method of claim 24 wherein said foot portion of said cover extends beyond one of said longitudinal edges of said absorbent member.

26. The method of claim 24 wherein said absorbent member has a length and said foot portion of said cover has a length which extends a distance of at least about 20 percent along the length of said absorbent member and said absorbent member and said cover are rolled up starting from said first end.

27. The method of claim 24 wherein said absorbent member has a length and said foot portion of said cover has a length which extends a distance of at least about 20 percent along the length of said absorbent member and said absorbent member and said cover are rolled up starting from said second end.

28. A method of forming a catamenial tampon comprising:
a) forming an absorbent ribbon having a rectangular configuration;
b) cutting said absorbent ribbon into individual absorbent members, each absorbent member having first and second ends and first and second longitudinal edges, and each of said longitudinal edges being of greater dimension than said ends;
c) positioning an absorbent member on a cover having an L-shaped configuration, said cover having a leg and a foot, said absorbent member and said cover being aligned such that a portion of said cover extends beyond one of said longitudinal edges of said absorbent member;

d) rolling said absorbent member and said cover in a longitudinal direction into a cylindrical softwind wherein said foot extends outward from said softwind and forms a flexible sheath, said flexible sheath spanning an arc of at least 360 degrees;

e) radially compressing said softwind into a pledget having an insertion end and a trailing end with said flexible sheath defining a protective finger sheath extending out from said trailing end; and f) rounding said insertion end of said pledget to facilitate insertion of said pledget into a body cavity.

29. The method of claim 28 wherein said absorbent member and said cover are rolled such that said protective finger sheath acquires a conical configuration having an apex positioned adjacent to said trailing end of said pledget.

\* \* \* \* \*